United States Patent [19]

Olmo et al.

[11] Plant 4,787

[45] Nov. 10, 1981

[54] TABLE GRAPE

[76] Inventors: Harold P. Olmo, Putah Creek Levee Rd.; Albert T. Koyama, 713 Hunt Way, both of Davis, Calif. 95616

[21] Appl. No.: 115,857

[22] Filed: Jan. 28, 1980

[51] Int. Cl.[3] ..... A01H 5/00

[52] U.S. Cl. ..... Plt./47

[58] Field of Search ..... Plt./47

*Primary Examiner*—James R. Feyrer

*Attorney, Agent, or Firm*—Townsend and Townsend

[57] ABSTRACT

A new and distinct variety of grapevine useful for production of table grapes superior to the Emperor variety in its higher and more consistent yields with short pruning systems, its earlier production of full color berries which are larger in size than Emperor and its ability to cold store for a long period in excellent condition.

3 Drawing Figures

This invention relates to a new and distinct variety of grapevine of the *vinifera* species to be used as a late harvest table grape, with exceptionally large seeded berries and having excellent characteristics for long conservation in cold storage, with an attractive red color.

The new variety is the result of the following cross, L12-80×S45-48. It was selected from a progeny of 298 seedlings planted at the Sierra Vista Ranch of the Di Giorgio Fruit Corporation, May 27, 1958. The new variety was then asexually reproduced from cuttings taken from the original seedling selection in Spring of 1964 at the Kearney Horticultural Field Station, Parlier, Calif. The variety has been tested at regional trials at the field station and at the University Vineyard, Davis, Calif., under the number 10-23D and the unique features of the new variety have been retained.

The derivation of the parental varieties is as follows:

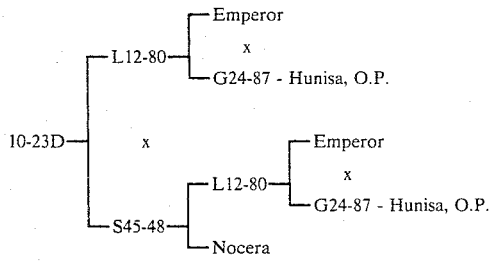

Figure 1:
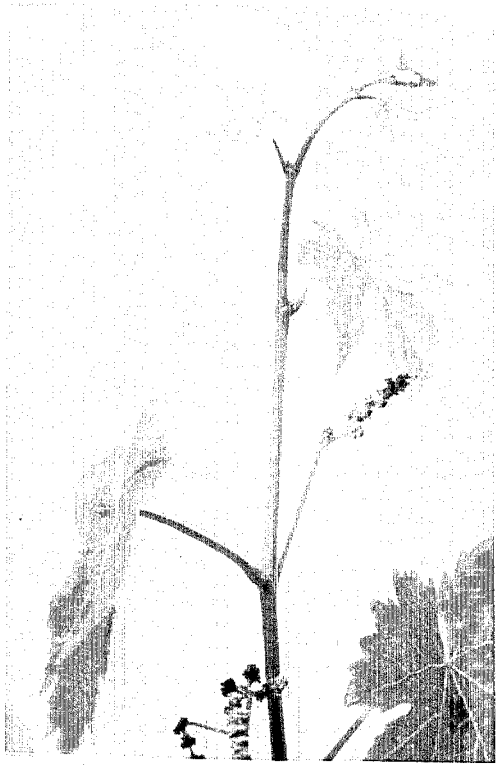
FIG. 1 is a drawing which illustrates a typical shoot tip of this variety.
Figure 3:
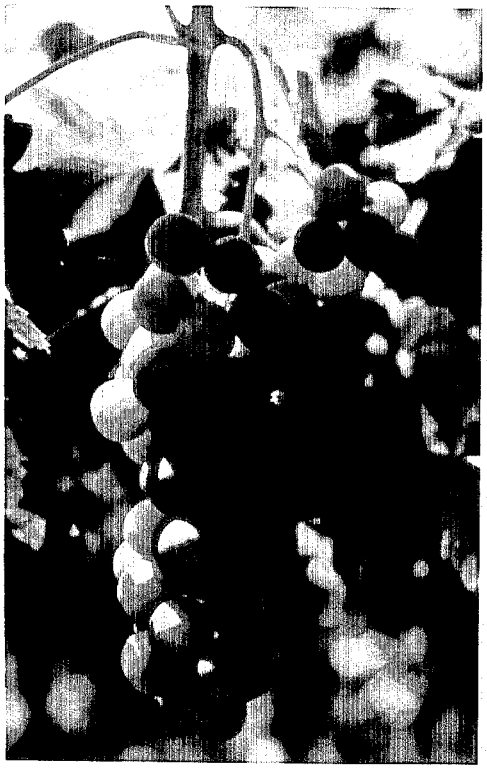
FIG. 3 is a drawing of a typical cluster of the new variety.
Figure 2:
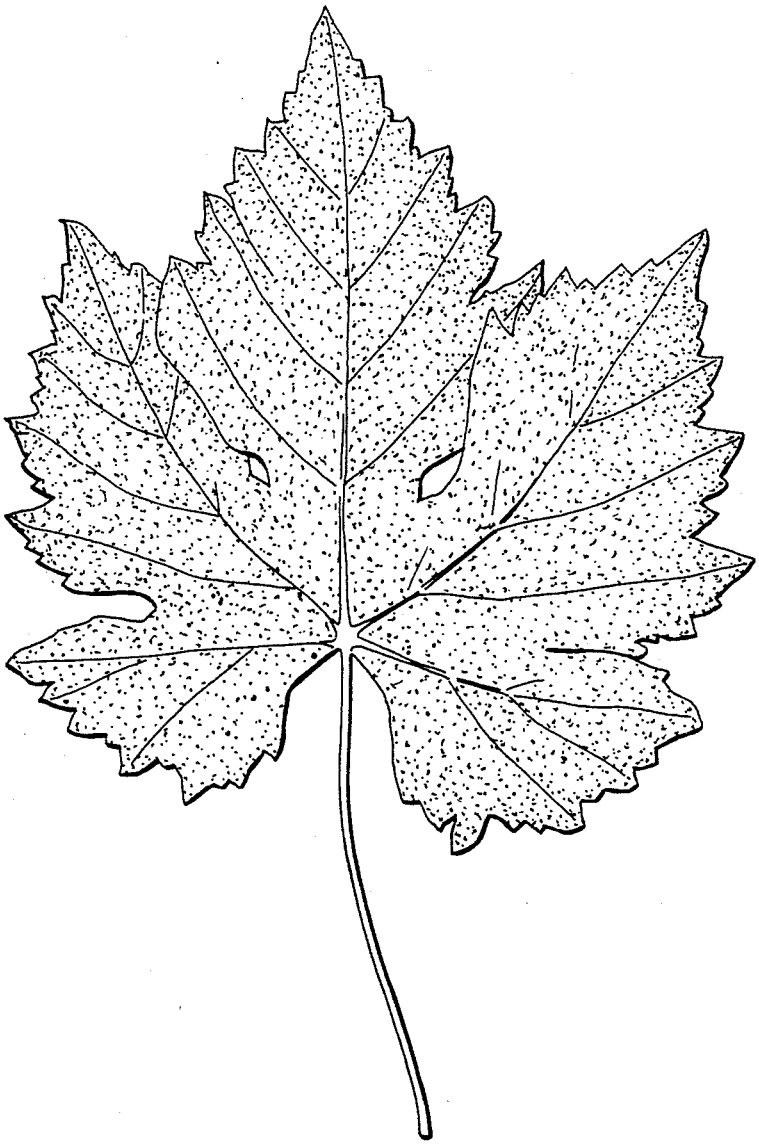
FIG. 2 is a drawing of a typical leaf of the new variety shown reduced from actual size.

The objectives in breeding this new variety were to obtain an improvement or addition to the Emperor class, the only red grape now utilized in California for long conservation in cold storage, extending the marketing season until the end of March. The Emperor occasionally gives poor yields, the fruit does not obtain full red coloration and the palatability is below average. Attractiveness of late storage grapes is also enhanced by large berry size as they are often utilized for table decoration during the holiday season.

The new variety is well adapted to supplement the Emperor and is best adapted for culture under the same type of soil and climatic conditions. It appears to be superior to Emperor in higher and consistent yields with short pruning systems, it produces full color earlier, has larger berry size and will also cold store for a long period in excellent condition. Because of exceptionally large berry size, firm flesh, and easy separation of the seeds, it can be sliced or diced for fruit salad.

The colors referred to in the following description under the heading Plant Characteristics are subject to substantial variation and are not considered distinctive or diagnostic features of the plant of this invention.

PLANT CHARACTERISTICS

The distinctive varietal characteristics of the novel plant described below in detail were observed during the first fruiting season and thereafter in trial plots at Davis and Parlier, Calif.

Vine: Less vigorous than Emperor, with slender and straight trunk, canes more numerous than Emperor, foliage canopy sparse, permitting uniform coloring of fruit without leaf removal before harvest. Bud burst late, few days before Emperor, leaf-fall late, autumn coloration bright yellow.

Shoot Tip (10"–12"): Summit strongly incurved, yellow-green, tinged bronze, laterals weakly developed, glabrous, shiny. First flat leaf three-lobed, very shiny surface, lightly bronzed, tips shiny.

Shoot: Very slender, narrow striations with punctate markings, faintly colored, light green, retains glossy appearance; tendrils very thin, wiry, bifid to trifid, bearing inflorescence at fifth node, occasionally a small additional one at node six; inflorescence very narrow with very slender peduncle, some calyptras drying at bloomtime (indehiscent); flower with very small pistil, stamens diverging, filaments rigid.

Cane: Numerous canes, more open, good wood maturity, light brown, darker near the nodes and exposed surfaces. Some striation noticeable, pith small, cross section round, buds small, pointed and sealed.

Leaf: Medium, blade length 17.1 cm., width 16.1 cm.; five-lobed major lateral lobes with ribs arched inward so that three major lobes overlap, closing the very deep sinuses to eyelets, central lobe short, less prominent than laterals, blade flat, smooth, retains some glossiness, glabrous; petiole 13.0 cm.; thin, 2 mm.; terminal teeth very large in contrast with lateral teeth, acute with very straight sides; inferior sinuses well marked, narrow, sometimes closed; petiolar sinus wide, open U-shaped.

Cluster: Large to very large, average 1017 gm., 31.3 cm. overall length from point of attachment, width 15.0 cm.; peduncle very long and very thin in diameter, 4 cm. from attachment to first tendril branch, plus 5 cm. to first branch of main rachis, usually straight and lignified (brown) about 1 cm. at base; well-filled to compact.

Berry: Very large, weight of 10 largest per cluster, 132.5 gm.; spherical to oblate, 29.6×26.9 mm.; skin surface somewhat fissured and blotched, thin and resistant; color strong purplish red 10RP 5/12 to deep purplish red 10RP 3/10 (Nickerson Color Fan); surface bloom moderate; skin rather thin but crack-resistant; brush very resistant to detachment, clear, broad, 4 mm×9 mm, round in cross section, vascular traces deep red; flesh firm and meaty in texture, bleached or milky in appearance at full maturity with sweet, neutral flavor; expressed juice is clear; chalaza small, shallow, crater-like; beak long, slender and tapered to sharp point, black-tipped at micropyle with remnant of attached vascular tissue, folds shallow; seed when air dried slender, 4 mm×9 mm, body triangular in cross-section; seeds large, 3 to 4 per berry, seed separate cleanly from the pulp, so berries can be easily sliced for salad; pedicel attachment to berry very strong, with exceptionally large and flanged torus, berry remaining intact and sealed for very long periods of cold storage.

We claim:

1. The new and distinct variety of table grape herein described and illustrated and identified by the characteristics enumerated above.

* * * * *